United States Patent
Dudycz et al.

(10) Patent No.: US 6,379,954 B1
(45) Date of Patent: *Apr. 30, 2002

(54) AMIDO AND PEPTIDO MODIFIED CATALYTIC OLIGONUCLEOTIDES

(75) Inventors: Lech Dudycz, Worcester, MA (US); Jasenka Matulic-Adamic, Boulder; Leonid Beigelman, Longmont, both of CO (US)

(73) Assignee: Ribozyme Pharmaceuticals, Incorporated, Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/494,722

(22) Filed: Jan. 31, 2000

Related U.S. Application Data

(63) Continuation of application No. 09/021,695, filed on Feb. 10, 1998, now Pat. No. 6,093,555, which is a continuation of application No. 08/357,577, filed on Dec. 16, 1994, now Pat. No. 5,783,425, which is a continuation-in-part of application No. 08/143,832, filed on Oct. 27, 1993, now abandoned.

(51) Int. Cl.$^7$ .............. C12N 5/06; C12N 5/08; C07H 21/00; C07H 21/02; A61K 31/712
(52) U.S. Cl. .............. 435/325; 435/91.31; 435/366; 536/24.3; 536/24.5
(58) Field of Search .............. 435/6, 91.1, 91.31, 435/325, 366, 375; 514/44; 536/23.1, 23.2, 24.3, 24.5, 25.3

(56) References Cited

U.S. PATENT DOCUMENTS 5,783,425 A * 7/1998 Dudycz et al. .......... 435/91.31
6,093,555 A * 7/2000 Dudycz et al. .......... 435/91.31

FOREIGN PATENT DOCUMENTS

WO 91/06556 * 5/1991

OTHER PUBLICATIONS

Christoffersen et al. "Robozymes as human therapeutic agents" J. Med. Chem. 38(12): 2023–2037, Jun. 1995.*
Ghosh et al. "Use of Maledimide–thiol coupling chemistry for efficient synthesis of oligonucleotide–enzyme conjugate hybridization probes" Bioconjugate Chem. 1(1): 71–77, Jan. 1990.*
Gura. "Antisense has growing pains" Science 270: 575–577, Oct. 1995.*
Gewirtz et al. Facilitating oligonucleotide delivery: Helping antisense deliver on its promise. Proc. Natl. Acad. Sci. 93: 3161–3163, Apr. 1996.*
Haralambidis et al. The solid phase synthesis of oligonucleotides containing a 3' peptide moiety. Tetrahedron Lett. 28: 5199–5202, Apr. 1996.*
Scaringe et al. Chemical synthesis of biologically active oligoribonucleotides using B–cyanoethyl protected ribonucleoside phosphoramidites. Nucleic Acids Res. 18:5433–5441, Jun. 1995.*
Stull et al. "Antigene, ribozyme and aptamer nucleic acid drug design: Progress and prospects" Pharm. Res. 12(4): 465–483, Apr. 1995.*
Rojanasakul, Y. Antisense oligonucleotide therapeutics: Drug delivery and targeting. Adv. Drug Delivery Rev. 18: 115–131, 1996.*
Antisense '97: A roundtable on the state of the industry. Nat. Biotechnol. 15: 519–524, Jun. 1997.*

* cited by examiner

Primary Examiner—Sean McGarry
Assistant Examiner—Thomas G Larson
(74) Attorney, Agent, or Firm—McDonnell Boehnen Hulbert & Berghoff

(57) ABSTRACT

Oligonucleotide comprising a nucleotide base having the formula:

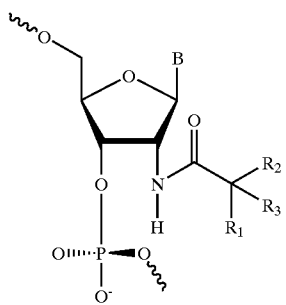

wherein B is a nucleotide base or hydrogen; $R_1$, $R_2$ and $R_3$ independently is selected from the group consisting of hydrogen, an alkyl group containing between 2 and 10 carbon atoms inclusive, an amine, an amino acid, and a peptide containing between 2 and 5 amino acids inclusive; and the zigzag lines are independently hydrogen or a bond.

10 Claims, 13 Drawing Sheets

THE HAMMERHEAD RIBOZYME

Fig. 2
*PRIOR ART*
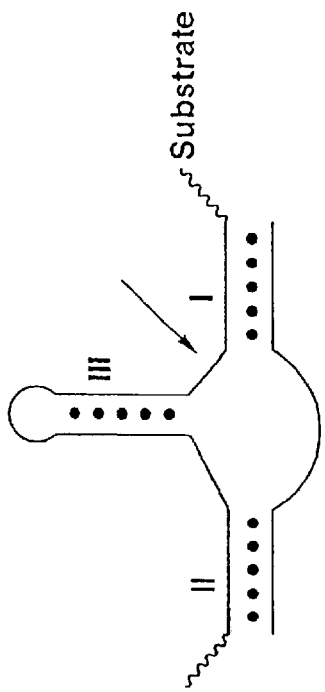
a
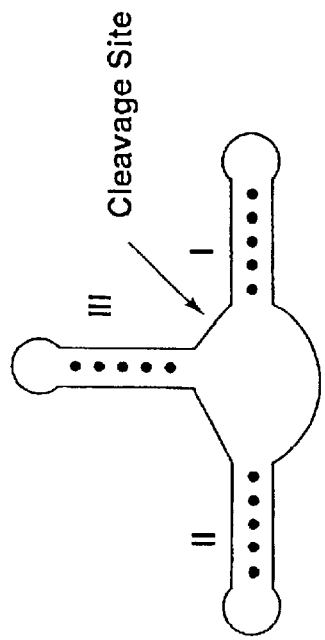
b
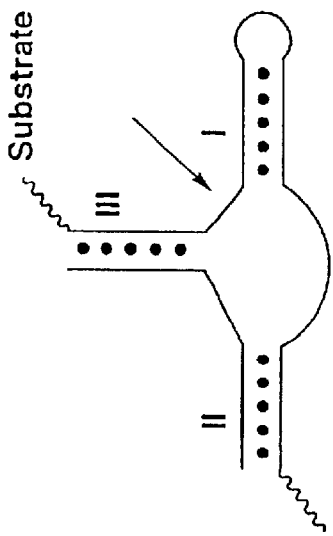
c
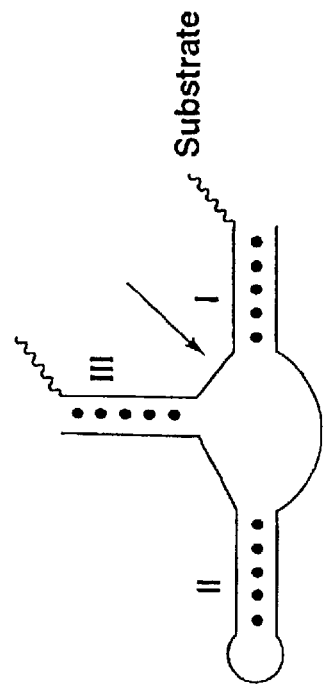
d

HEPATITIS DELTA VIRUS RIBOZYME

Fig. 5
PRIOR ART

NEUROSPORA VS RNA ENZYME

Figure 6: N-aminoacyl conjugates of 2'-d-2'-aminouridine

Fig. 7: Deprotection of aspartyl conjugate under standard oligonucleotide deprotection conditions:

Figure 8: Hammerhead Ribozyme to Site A (HHA)

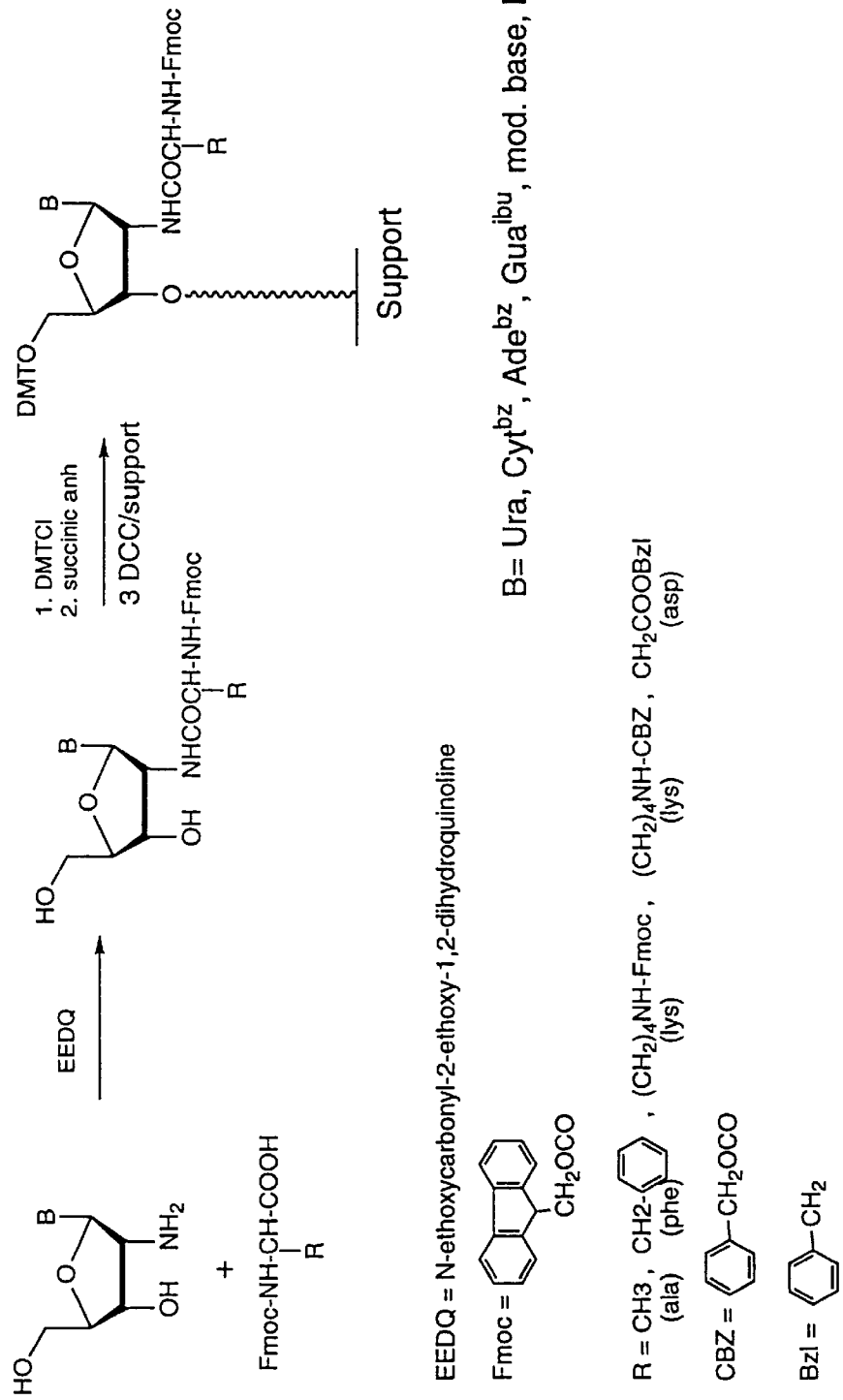
Figure 10 A: N-aminoacyl conjugates of 2'-d-2'-aminonucleosides for 3'-end derivatisation

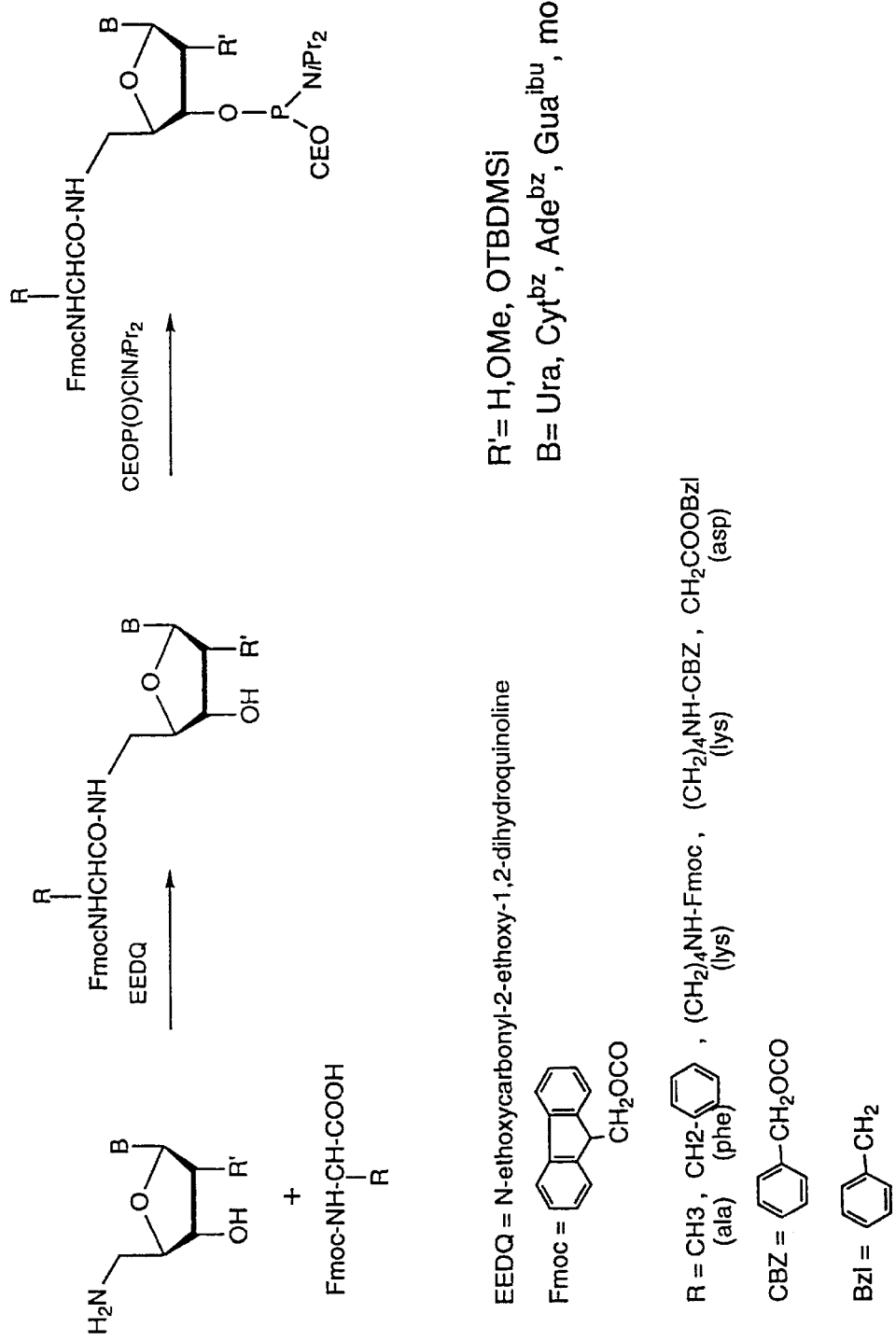

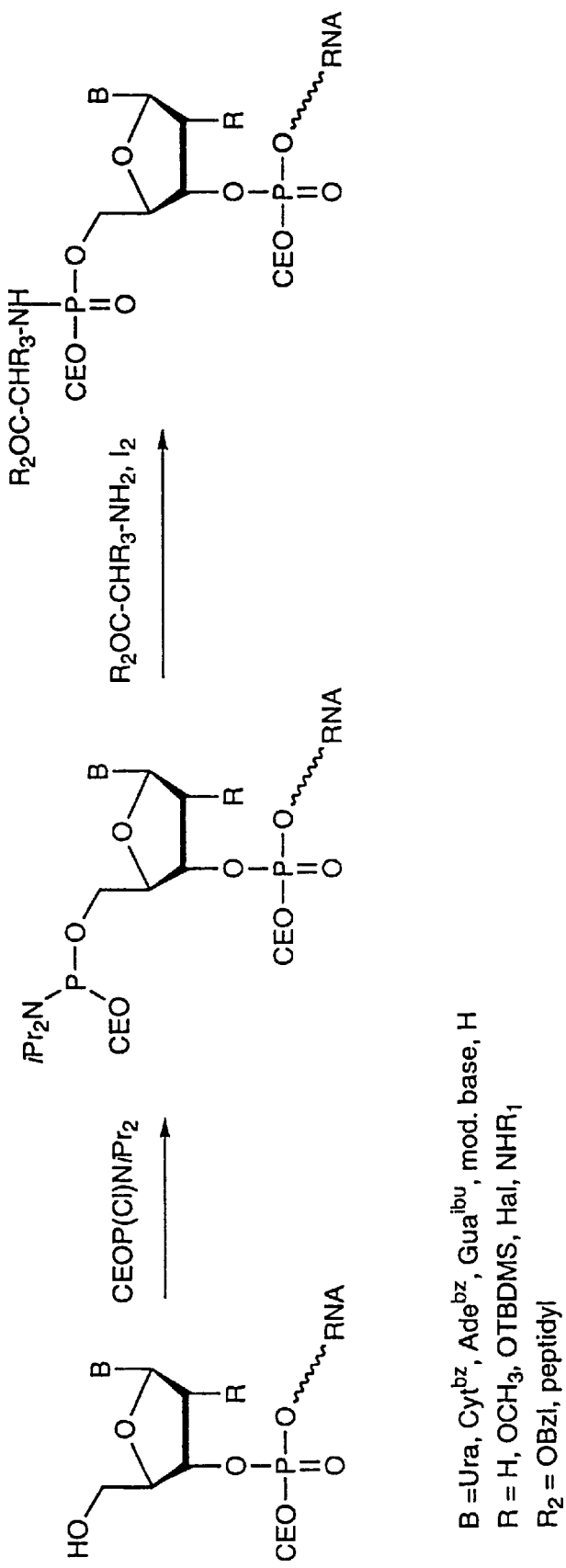
Fig. 11B: Synthesis of oligonucleotide 5'-phosphoramidates

AMIDO AND PEPTIDO MODIFIED CATALYTIC OLIGONUCLEOTIDES

This application is a continuation of U.S. Ser. No. 09/021,695 filed Feb. 10, 1998, now U.S. Pat. No. 5,093,555, which is a continuation of Ser. No. 08/357,577, filed Dec. 16, 1994, now U.S. Pat. No. 5,783,425 which is a continuation-in-part of Dudycz, entitled "2'-amido and 2'-peptido modified oligonucleotides", U.S. Ser. No. 08/143,832 filed Oct. 27, 1993, now abandoned, the whole of which, including drawings, is hereby incorporated by reference herein.

BACKGROUND OF THE INVENTION

This invention relates to modifications of oligonucleotides.

Usman et al., "Nucleozymes", International Application No. PCT/US 93/00833, describes modification of the 2'-hydroxyl group of RNA to produce modified nucleotides. Such nucleotides are termed nucleic acid analogs, and may have a "good coordinating ligand" with divalent metal ions, e g, a halogen, or amine group. Acyclic analogs are also described.

Eckstein, International Application No. PCT/EP91/01811 (WO 92/07065), describes 2'-hydroxyl modifications of RNA having the following substitutions in place of the hydroxyl group: halo, sulfhydryl, azido, amino, mono-substituted amino and di-substituted amino.

Sproat et al., 1994 "Synthetic catalytic oligonucleotide structures", U.S. Pat. No. 5,334,711, describes hammerhead ribozymes which contain nucleotides having 2'-OR modifications where, O represents oxygen and R represents H, or alkyl, alkenyl, or alkinyl.

Buhr and Matteucci, International Application No. WO 91/06556, describes 2'-hydroxyl modifications of antisense oligonucleotides with NHAC modifications.

SUMMARY OF THE INVENTION

This invention relates to replacement of the 2'-hydroxyl group of a ribonucleotide moiety with a 2'-amido or 2'-peptido moiety. In other embodiments, the 3' and 5' portions of the sugar of a nucleotide may be substituted, or the phosphate group may be substituted with amido or peptido moieties. Generally, such a nucleotide has the general structure shown in Formula I below:

FORMULA I

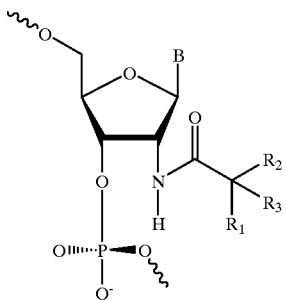

The base (B) is any one of the standard bases or is a modified nucleotide base known to those in the art, or can be a hydrogen group. In addition, either $R_1$ or $R_2$ is H or an alkyl, alkene or alkyne group containing between 2 and 10 carbon atoms, or hydrogen, an amine (primary, secondary or tertiary, e.g., $R_3NR_4$ where each $R_3$ and $R_4$ independently is hydrogen or an alkyl, alkene or alkyne having between 2 and 10 carbon atoms, or is a residue of an amino acid, i.e., an amide), an alkyl group, or an amino acid (D or L forms) or peptide containing between 2 and 5 amino acids. The zigzag lines represent hydrogen, or a bond to another base or other chemical moiety known in the art. Preferably, one of $R_1$, $R_2$ and $R_3$ is an H, and the other is an amino acid or peptide.

Applicant has recognized that RNA can assume a much more complex structural form than DNA because of the presence of the 2'-hydroxyl group in RNA. This group is able to provide additional hydrogen bonding with other hydrogen donors, acceptors and metal ions within the RNA molecule. Applicant now provides molecules which have a modified amine group at the 2' position, such that significantly more complex structures can be formed by the modified oligonucleotide. Such modification with a 2'-amido or peptido group leads to expansion and enrichment of the side-chain hydrogen bonding network. The amide and peptide moieties are responsible for complex structural formation of the oligonucleotide and can form strong complexes with other bases, and interfere with standard base pairing interactions. Such interference will allow the formation of a complex nucleic acid and protein conglomerate.

Oligonucleotides of this invention are significantly more stable than existing oligonucleotides and can potentially form biologically active bioconjugates not previously possible for oligonucleotides. They may also be used for in vitro selection of unique aptamers, that is, randomly generated oligonucleotides which can be folded into an effective ligand for a target protein, nucleic acid or polysaccharide.

Thus, in a first aspect, the invention features an oligonucleotide containing the modified base shown in Formula I, above.

In other aspects, the oligonucleotide may include a 3' or 5' nucleotide having a 3' or 5' located amino acid or aminoacyl group. In all these aspects, as well as the 2'-modified nucleotide, it will be evident that various standard modifications can be made. For example, an "O" may be replaced with an S, the sugar may lack a base (i.e., abasic) and the phosphate moiety may be modified to include other substitutions (see Sproat, supra).

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1 is a diagrammatic representation of the hammerhead ribozyme domain known in the art. Stem II can be $\geq 2$ base-pair long.

FIGS. 2A–2D:

FIG. 2a is a diagrammatic representation of the hammerhead ribozyme domain known in the art; FIG. 2b is a diagrammatic representation of the hammerhead ribozyme as divided by Uhlenbeck (1987, Nature, 327, 596–600) into a substrate and enzyme portion; FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, Nucl. Acids. Res., 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H ,refers to bases A, U or C. Y refers to pyrimidine bases.

FIG. 5 is a representation of the general structure of the self-cleaving VS RNA ribozyme domain.

FIGS. 7A & B describe a method for deprotection of oligonucleotides containing a 2'-hydroxyl group modification of the present invention.

Figure 8:
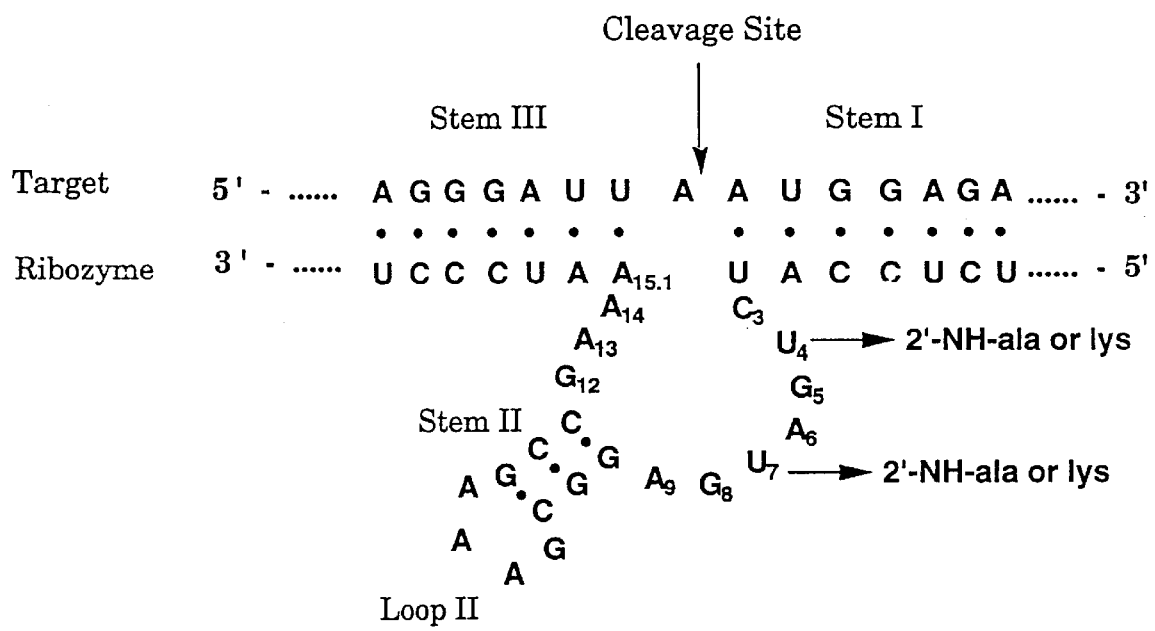

FIG. 8 is a diagrammatic representation of a hammerhead ribozyme targeted to site A. Positions of 2'-hydroxyl group substitution is indicated.

Figure 9:
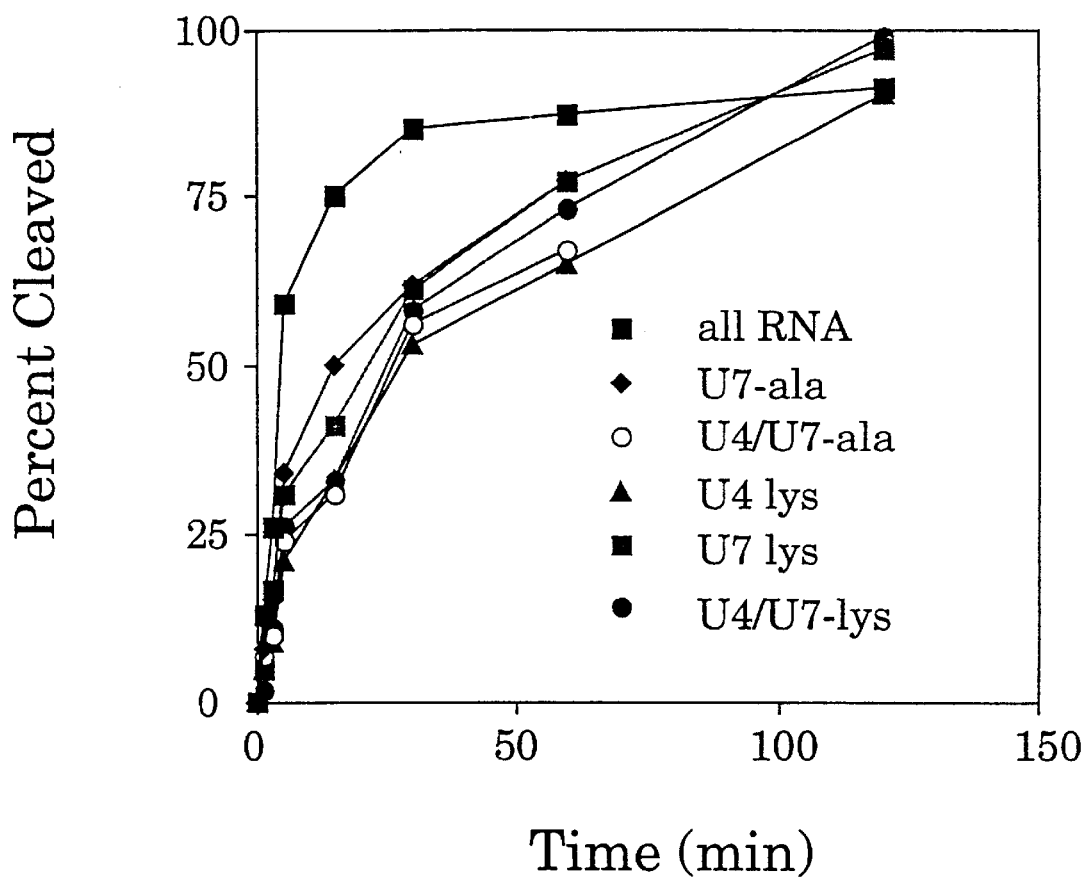

FIG. 9 shows RNA cleavage activity of ribozymes containing a 2'-hydroxyl group modification of the present invention. All RNA, represents hammerhead ribozyme (HHA) with no 2'-hydroxyl group modifications. U7-ala, represents HHA ribozyme containing 2'-NH-alanine modification at the U7 position. U4/U7-ala, represents HHA containing 2'-NH-alanine modifications at U4 and U7 positions. U4 lys, represents HHA containing 2'-NH-lysine modification at U4 position. U7 lys, represents HHA containing 2'-NH-lysine modification at U7 position. U4/U7-lys, represents HHA containing 2'-NH-lysine modification at U4 and U7 positions.

FIGS. 10A & B are a schematic representation of synthesizing (solid-phase synthesis) 3' ends of RNA with modification of the present invention. B, refers to either a base, modified base or an H.

FIGS. 11A & B are a schematic representation of synthesizing (solid-phase synthesis) 5' ends of RNA with modification of the present invention. B, refers to either a base, modified base or an H.

Oligonucleotides of this invention are described generally above, and the structure is shown in Formula I, where such modifications to the 2'-hydroxyl group can be made in one or more positions of an RNA or DNA molecule. Preferably, the oligonucleotide is single-stranded and has between 10 and 50 bases of which one or more may be modified as shown, preferably, between 1 and 10 are modified. Such oligonucleotides may include those having enzymatic activity, ie., ribozymes, which are modified in the 2'- position of the sugar moiety as shown in Formula I to provide stability to that enzymatic activity without significant alteration of the activity.

Oligonucleotides of the present invention can be readily synthesized using carbamate protecting groups, such as F-moc, in the peptide moieties and deprotected under mild basic conditions. Such nucleotides can then be incorporated by standard solid-phase synthesis using nucleoside phosphoramidite or H-phosphonate intermediates.

Uses

The above nucleotides are particularly useful in ribozymes. Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein.

After a ribozyme has bound and cleaved its RNA target it is released from that RNA to search for another target and can repeatedly bind and cleave new targets.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein.

After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to inter-molecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target RNAs such that specific treatment of a disease or condition can be provided with either one or several enzymatic nucleic acids. Such enzymatic nucleic acid molecules can be delivered exogenously to specific cells as required.

Synthesis of Ribozymes

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure.

The ribozymes are chemically synthesized. The method of synthesis used follows the procedure for normal RNA synthesis as described in 30 Usman et al., 1987 *J. Am. Chem. Soc.*, 109, 7845 and in Scaringe et al., 1990 *Nucleic Acids Res.*, 18, 5433 and makes use of common nucleic acid protecting and coupling groups, such as dimethoxytrityl at the 5'-end, and phosphoramidites at the 3'-end. The average stepwise coupling yields were >98%.

Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

Various modifications to ribozyme structure can be made to enhance the utility of ribozymes. Such modifications will enhance shelf-life, half-life in vitro, stability, and ease of introduction of such ribozymes to the target site, eg., to enhance penetration of cellular membranes, and confer the ability to recognize and bind to targeted cells.

Optimizing Ribozyme Activity

Ribozyme activity can be optimized as described by Stinchcomb et al., "Method and Composition for Treatment of Restenosis and Cancer Using Ribozymes," filed May 18, 1994, U.S. Ser. No. 08/245,466. The details will not be repeated here, but include altering the length of the ribozyme binding arms (stems I and II, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules. Modifications which enhance their efficacy in cells, and removal of stem II bases to shorten RNA synthesis times and reduce chemical requirements. (All these publications are hereby incorporated by reference herein.).

Administration of Ribozyme

Sullivan et al., PCT WO94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

EXAMPLE 1

Figure 6:
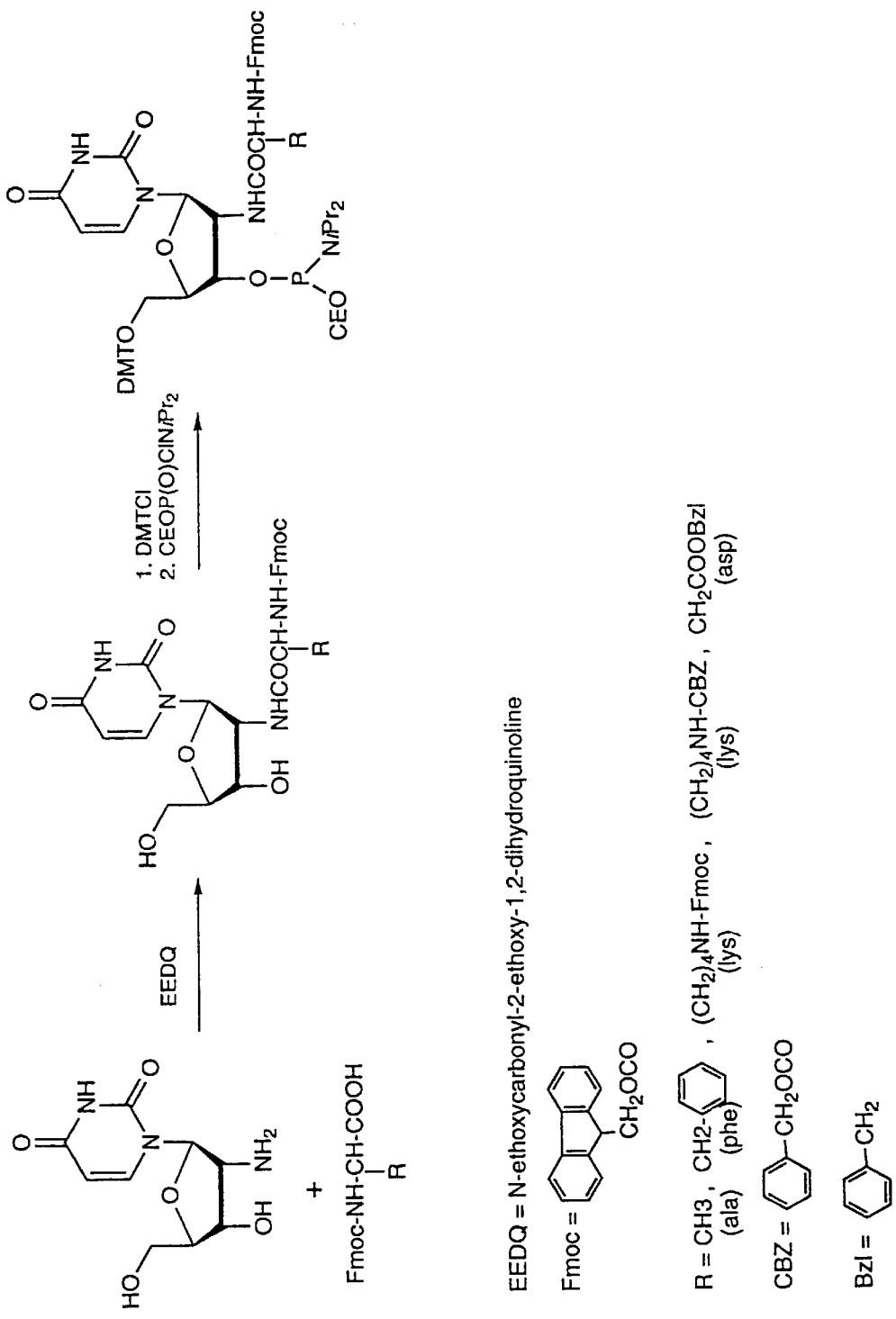
FIG. 6 is a schematic representation of synthesizing RNA phosphoramidite of a nucleotide containing a 2'-hydroxyl group modification of the present invention.

General Procedure for the Preparation of 2'-aminoacyl-2'-deoxy-2'-Aminonucleoside Conjugates Referring to FIG. 6, to the solution of 2'-deoxy-2'-amino nucleoside (1 mmol) and N-Fmoc L- (or D-) amino acid (1 mmol) in methanol [dimethylformamide (DMF) and tetrahydrofuran (THF) can also be used], 1-ethoxycarbonyl-2-ethoxy-1,2-dihydroquinoline (EEDQ) [or 1-isobutyloxycarbonyl-2-isobutyloxy-1,2-dihydroquinoline (IIDQ)] (2 mmol) is added and the reaction mixture is stirred at room temperature or up to 50° C. from 3–48 hours. Solvents are removed under reduced pressure and the residual syrup is chromatographed on the column of silicagel using 1–10% methanol in dichloromethane. Fractions containing the product are concentrated yielding a white foam with yields ranging from 85 to 95%. Structures are confirmed by 1H NMR spectra of conjugates which show correct chemical shifts for nucleoside and aminoacyl part of the molecule. Further proofs of the structures are obtained by cleaving the aminoacyl protecting groups under appropriate conditions and assigning $^1$H NMR resonances for the fully deprotected conjugate.

Partially protected conjugates described above are converted into their 5'-O-dimethoxytrityl derivatives and into 3'-phosphoramidites using standard procedures (Oligonucleotide Synthesis: A Practical Approach, M. J. Gait ed.; IRL Press, Oxford, 1984). Incorporation of these phosphoramidites into RNA was performed using standard protocols (Usman et al., 1987 supra).

Figure 7:
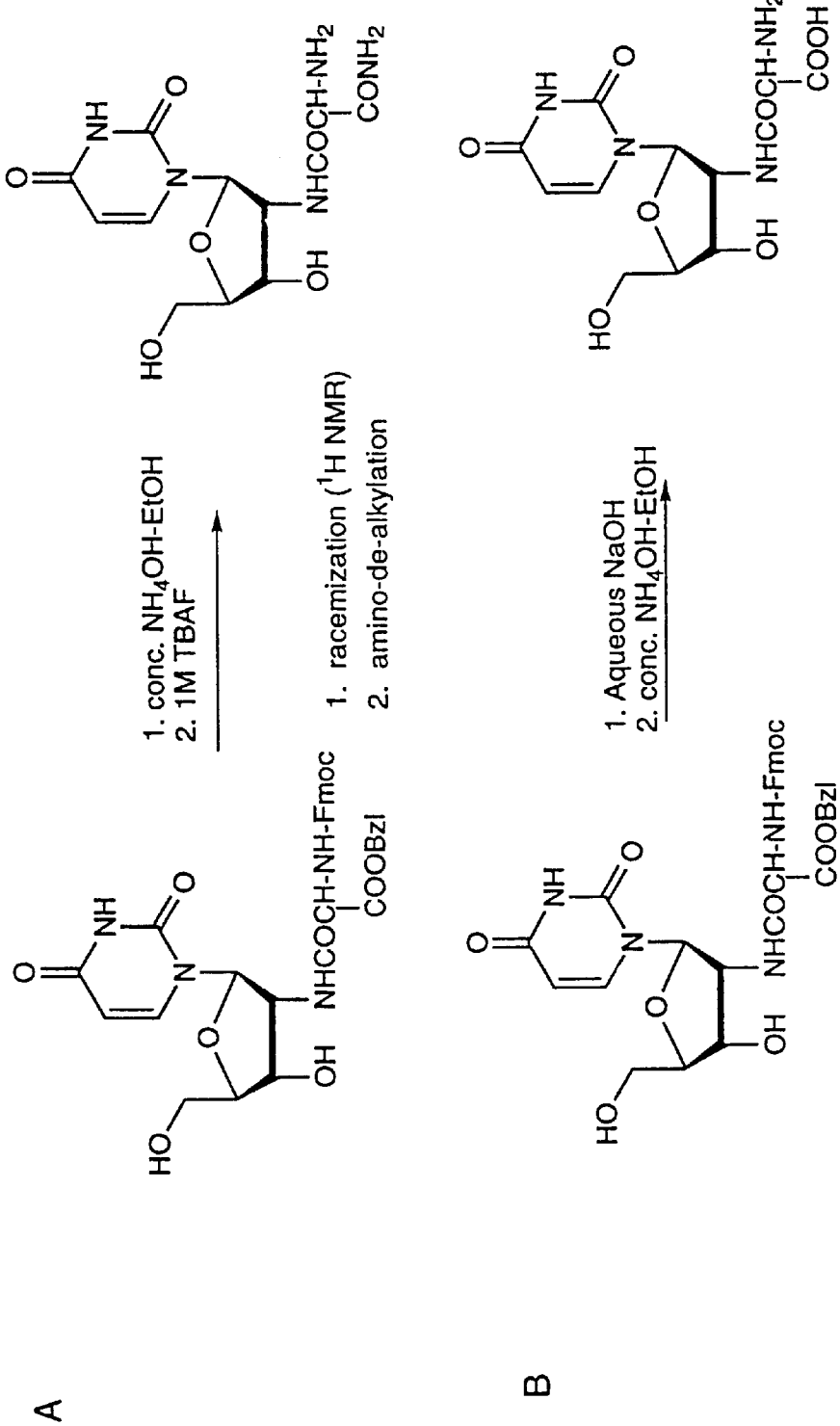

A general deprotection protocol for oligonucleotides of the present invention is described in FIG. 7.

The scheme shows synthesis of conjugate of 2'-d-2'-aminouridine. This is meant to be a non-limiting example, and those skilled in the art will recognize that, variations to the synthesis protocol can be readily generated to synthesize other nucleotides (e.g., adenosine, cytidine, guanosine) and/or abasic moieties.

EXAMPLE 2

RNA Cleavage by Hammerhead Ribozymes Containing 2'-aminoacyl Modifications

Hammerhead ribozymes targeted to site A (see FIG. 8) are synthesized using solid-phase synthesis, as described above. U4 and U7 positions are modified, individually or in combination, with either 2'-NH-alanine or 2'-NH-lysine.

RNA cleavage assay in vitro: Substrate RNA is 5' end-labeled using [γ-$^{32}$P] ATP and T4 polynucleotide kinase (US Biochemicals). Cleavage reactions were carried out under ribozyme "excess" conditions. Trace amount (≦1 nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM MgCl$_2$. The reaction is initiated by mixing the ribozyme and substrate solutions and incubating at 37° C. Aliquots of 5 μl are taken at regular intervals of time and the reaction is quenched by mixing with equal volume of 2x formamide stop mix. The samples are resolved on 20% denaturing polyacrylamide gels. The results are quantified and percentage of target RNA cleaved is plotted as a function of time.

Referring to FIG. 9, hammerhead ribozymes containing 2'-NH-alanine or 2'-NH-lysine modifications at U4 and U7 positions cleave the target RNA efficiently.

Sequences listed in FIG. 8 and the modifications described in FIG. 9 are meant to be non-limiting examples. Those skilled in the art will recognize that variants (base-substitutions, deletions, insertions, mutations, chemical modifications) of the ribozyme and RNA containing other 2'-hydroxyl group modifications, including but not limited to amino acids, peptides and cholesterol, can be readily generated using techniques known in the art, and are within the scope of the present invention.

EXAMPLE 3

Aminoacylation of 3'-Ends of RNA

Figure 3:
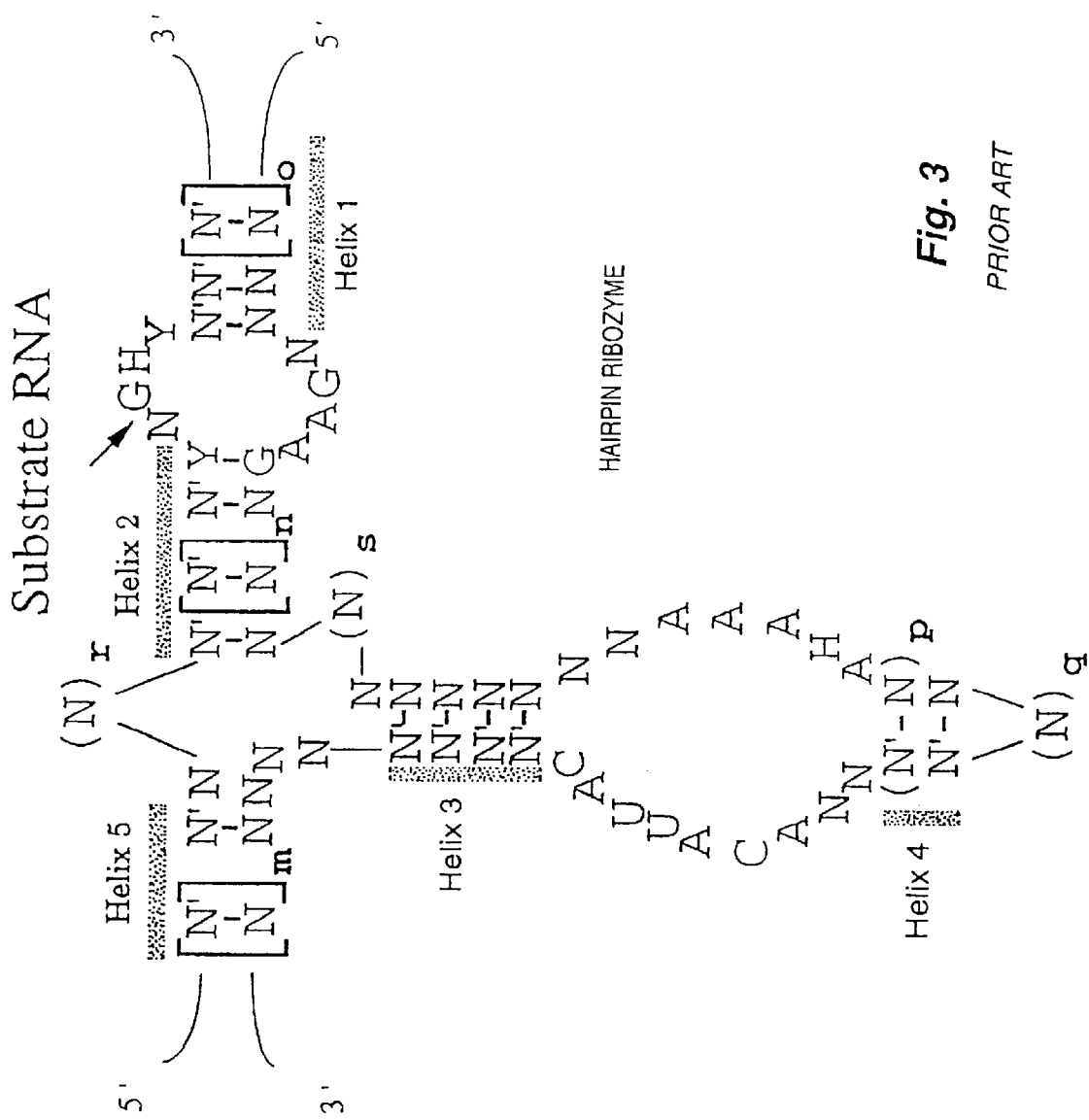

I. Referring to FIG. 10A, 3'-OH group of the nucleotide is converted to succinate as described by Gait, supra. This can be linked with amino-alkyl solid support (for example: CpG). Zig-zag line indicates linkage of 3' OH group with the solid support.

II. Preparation of Aminoacyl-derivatized Solid Support
A) Synthesis of O-Dimethoxytrityl (O-DMT) Amino Acids Referring to FIG. 10B, to a solution of L- (or D-) serine, tyrosine or threonine (2 mmol) in dry pyridine (15 ml) 4,4'-dimethoxytrityl chloride (3 mmol) is added and the reaction mixture is stirred at RT (about 20–25° C.) for 16 h. Methanol (10 ml) is then added and the solution evaporated under reduced pressure. The residual syrup was partitioned between 5% aq.

NaHCO$_3$ and dichloromethane, organic layer was washed with brine, dried (Na$_2$SO$_4$) and concentrated in vacuo. The residue is purified by flash silicagel column chromatography using 2–10% methanol in dichloromethane (containing 0.5% pyridine). Fractions containing product are combined and concentrated in vacuo to yield white foam (75–85% yield).

B) Preparation of the Solid Support and its Derivatization with Amino Acids

Figure 10B:
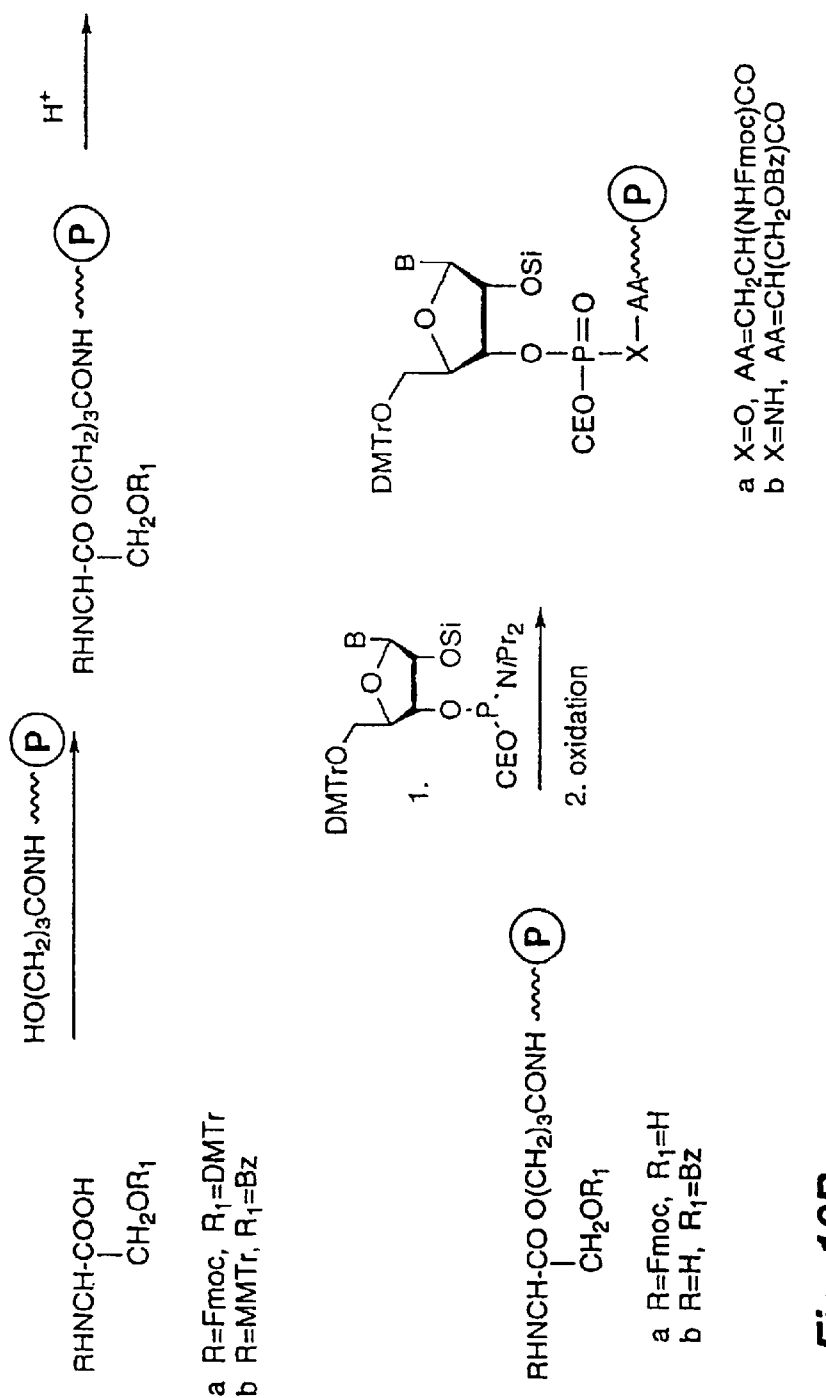

Referring to FIG. 10B, the modified solid support (has an OH group instead of the standard NH$_2$ end group) was prepared according to Haralambidis et al., Tetrahedron Lett. 1987, 28, 5199, (P denotes aminopropyl CPG or polystyrene type support). O-DMT or NH-monomethoxytrityl (NH-MMT amino acid was attached to the above solid support using standard procedures for derivatization of the solid support (Gait, 1984, supra) creating a base-labile ester bond between amino acids and the support. This support is suitable for the construction of RNA/DNA chain using suitably protected nucleoside phosphoramidites.

EXAMPLE 4

Aminoacylation of 5'-Ends of RNA

Figure 5:
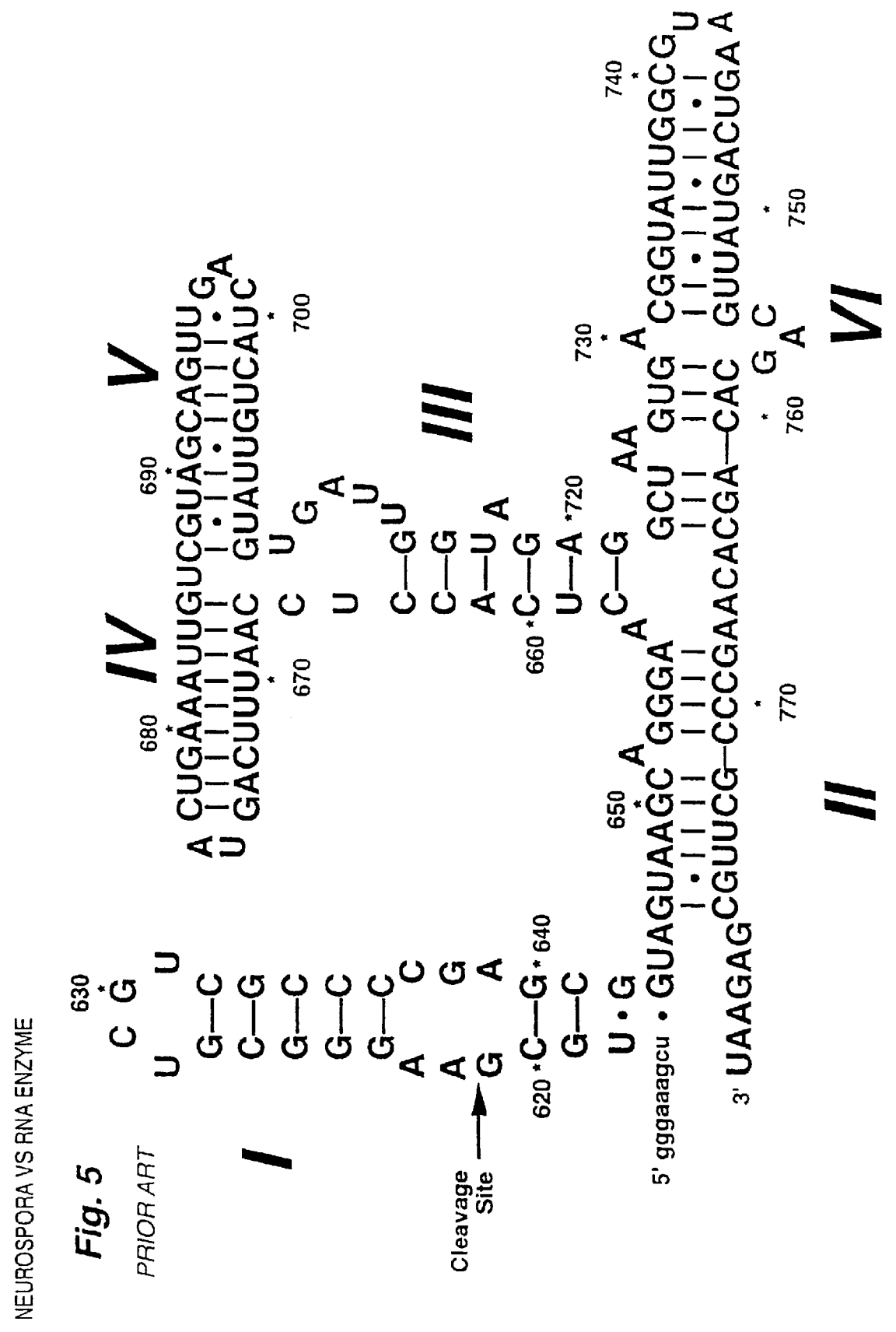

I. Referring to FIG. 11A, 5'-amino-containing sugar moiety was synthesized as described (Mag and Engels, 1989 *Nucleic Acids Res.* 17, 5973). Aminoacylation of the 5'-end of the monomer was achieved as described above and RNA phosphoramidite of the 5'-aminoacylated monomer was prepared as described by Usman et al., 1987 supra. The phosphoramidite was then incorporated at the 5E-end of the oligonucleotide using standard solid-phase synthesis protocols described above.

II. Referring to FIG. 11B, aminoacyl group(s) is attached to the phosphate group at the 5'-end of the RNA using standard procedures described above.

Diagnostic Uses

Ribozymes of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with target related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

TABLE I-continued

Characteristics of Ribozymes

Hammerhead Ribozyme

Figure 1:
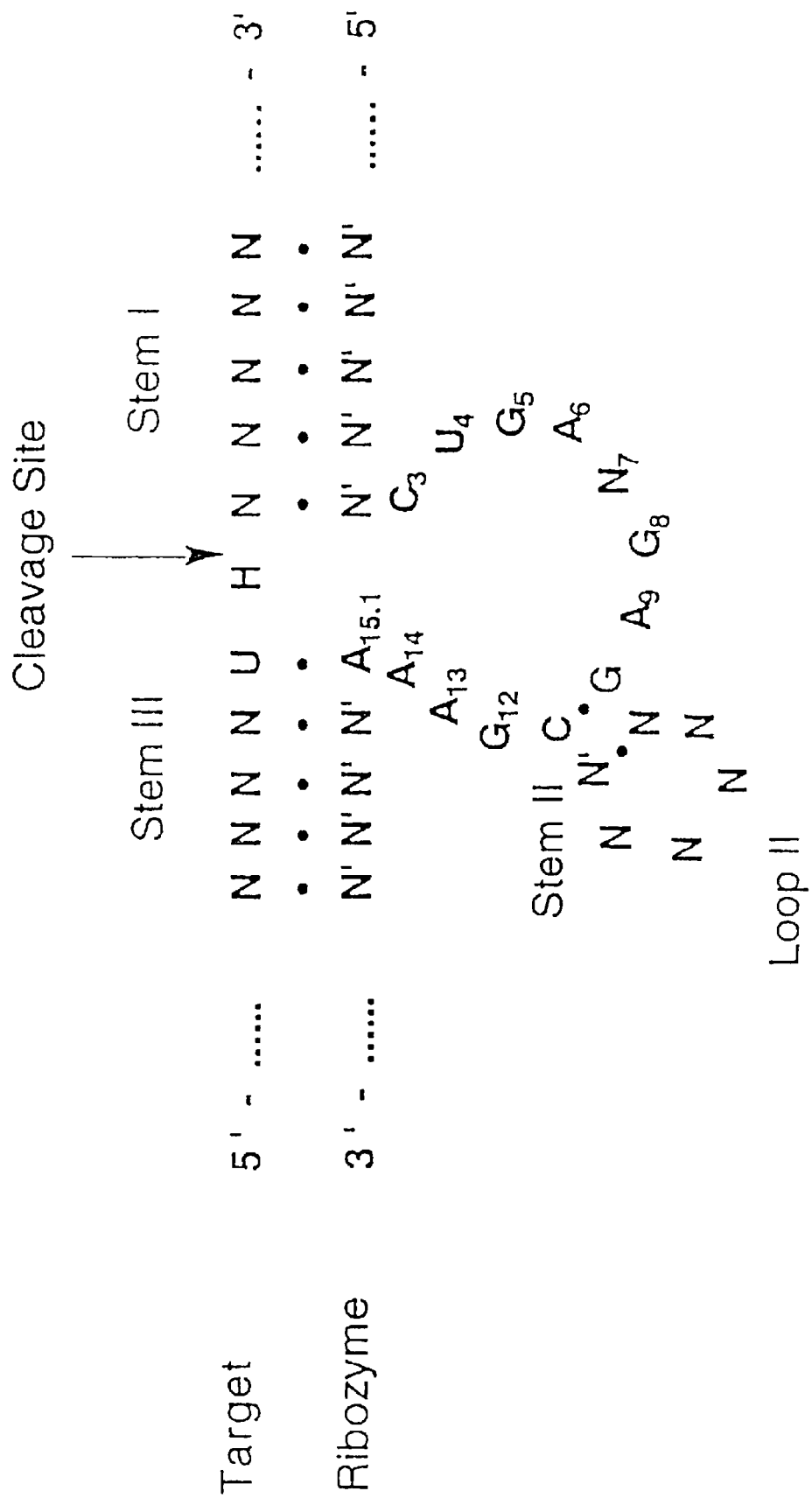
Figure 4:
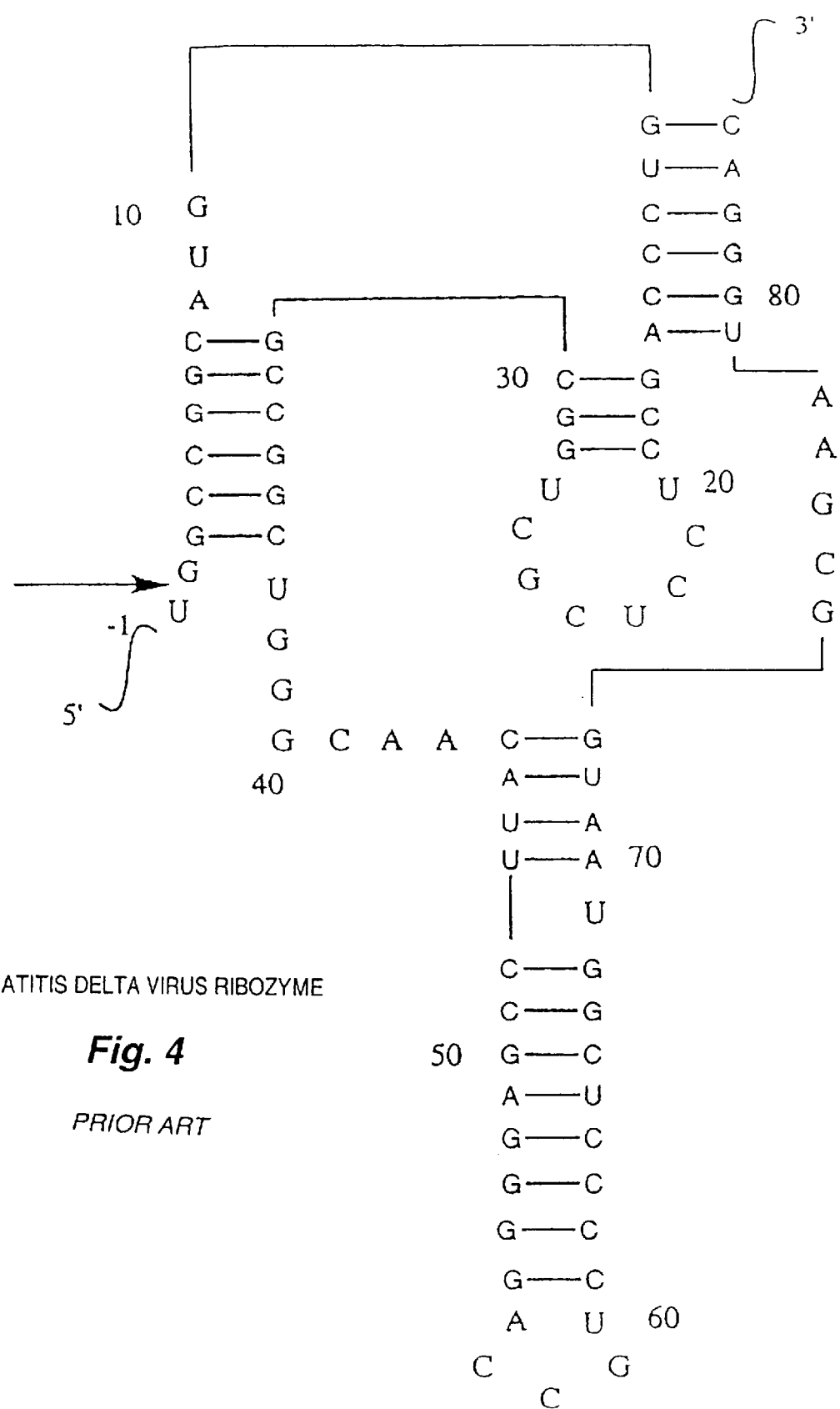
FIG. 4 is a representation of the general structure of the hepatitis delta virus ribozyme domain known in the art.

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2)
Hairpin Ribozyme Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).
Neuraspora VS RNA Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neuraspora VS RNA (FIG. 5).

What is claimed is:
1. An oligonucleotide with enzymatic activity, wherein the oligonucleotide is between 10 and 1000 nucleotides long and comprises a moiety having the formula I:

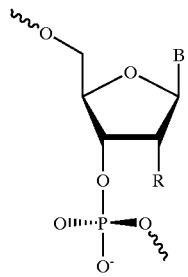

wherein B is a nucleotide base or hydrogen; R is selected from the group consisting of an aminoacyl group, and a $NHR_4$ group, wherein said $R_4$ is independently selected from the group consisting, of a peptidyl group containing between 2 and 5 amino acids inclusive, and $CO-CR_1R_2R_3$, wherein $R_1$, $R_2$ and $R_3$ independently is selected from the group consisting of hydrogen an alkyl group containing between 2 and 10 carbon atoms inclusive, and an alkyl amine; and the zigzag lines are independently hydrogen or a bond.

2. The oligonucleotide of claim 1, wherein said oligonucleotide is a ribozyme.

3. The oligonucleotide of claim 2, wherein said oligonucleotide is in a hammerhead motif.

4. A mammalian cell comprising the oligonucleotide of claim 1.

5. The mammalian cell of claim 4, wherein said mammalian cell is a human cell.

6. The oligonucleotide of claim 1, wherein said oligonucleotide further comprises a sugar modification other than that of formula I.

7. The oligonucleotide of claim 1, wherein said oligonucleotide further comprises a base modification.

8. The oligonucleotide of claim 1, wherein said oligonucleotide further comprises a phosphate modification.

9. The oligonucleotide of claim 1, wherein said oligonucleotide is between 10 and 50 nucleotides long.

10. The oligonucleotide of claim 1, wherein said oligonucleotide cleaves a separate RNA.

* * * * *